US012697440B2

(12) United States Patent
Gerken

(10) Patent No.: US 12,697,440 B2
(45) Date of Patent: Aug. 4, 2026

(54) MONITORING SYSTEM AND METHOD

(71) Applicant: Sanofi-Aventis Deutschland GMBH, Frankfurt am Main (DE)

(72) Inventor: Till Gerken, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 40 days.

(21) Appl. No.: 17/138,273

(22) Filed: Dec. 30, 2020

(65) Prior Publication Data

US 2021/0330889 A1 Oct. 28, 2021

Related U.S. Application Data

(63) Continuation of application No. 15/320,156, filed as application No. PCT/EP2015/064348 on Jun. 25, 2015, now Pat. No. 10,909,217.

(30) Foreign Application Priority Data

Jun. 27, 2014 (EP) ..................................... 14174717

(51) Int. Cl.
*A61M 5/315* (2006.01)
*A61M 5/31* (2006.01)
(Continued)

(52) U.S. Cl.
CPC ........ *A61M 5/31548* (2013.01); *G16H 20/10* (2018.01); *G16H 20/17* (2018.01);
(Continued)

(58) Field of Classification Search
CPC .......... A61M 5/31548; A61M 5/31553; A61M 2005/3126; A61M 2205/3561;
(Continued)

(56) References Cited

U.S. PATENT DOCUMENTS 8,808,228 B2 8/2014 Brister et al.
2008/0262469 A1* 10/2008 Brister et al.
(Continued)

FOREIGN PATENT DOCUMENTS

CN 102427840 4/2012
EP 2674181 12/2013
(Continued)

OTHER PUBLICATIONS

PCT International Preliminary Report on Patentability in International Application No. PCT/EP2015/064348, dated Dec. 27, 2016, 8 pages.
(Continued)

*Primary Examiner* — Fonya M Long
*Assistant Examiner* — William T. Monticello
(74) *Attorney, Agent, or Firm* — Fish & Richardson P.C.

(57) ABSTRACT

A monitoring system comprises:
  a first device (2) configured to
    capture an image of a medicament dosage indicated by a medicament dispensing device by an image capturing component of the first device;
    display the image of the medicament dosage on a display (21) of the first device; and
    transmit data representing the image of the medicament dosage to a second device; and
  computer code that when executed by a second device causes the second device (100) to:
    receive the data representing the image of the medicament dosage sent by the first device (2);
    perform optical character recognition on the data of the medicament dosage thereby to identify the dosage indicated by the medicament dispensing device; and
(Continued)

make a non-transient record of dosage information based at least in part on the identified medicament dosage.

21 Claims, 7 Drawing Sheets

(51) Int. Cl.

| | |
|---|---|
| *G16H 10/60* | (2018.01) |
| *G16H 20/10* | (2018.01) |
| *G16H 20/17* | (2018.01) |
| *G16H 40/67* | (2018.01) |

(52) U.S. Cl.
CPC ..... *G16H 40/67* (2018.01); *A61M 2005/3126* (2013.01); *A61M 5/31553* (2013.01); *A61M 2205/3561* (2013.01); *A61M 2205/3592* (2013.01); *A61M 2205/50* (2013.01); *A61M 2205/505* (2013.01); *A61M 2205/52* (2013.01); *A61M 2205/581* (2013.01); *A61M 2205/582* (2013.01); *A61M 2205/8206* (2013.01); *G16H 10/60* (2018.01)

(58) Field of Classification Search
CPC ...... A61M 2205/3592; A61M 2205/50; A61M 2205/505; A61M 2205/52; A61M 2205/581; A61M 2205/582; A61M 2205/8206; G16H 20/17; G16H 40/67; G16H 20/10; G16H 10/60
See application file for complete search history.

(56) References Cited

U.S. PATENT DOCUMENTS

| | | | |
|---|---|---|---|
| 2008/0306444 | A1 * | 12/2008 | Brister et al. |
| 2010/0204596 | A1 | 8/2010 | Knutsson |
| 2010/0286612 | A1 | 11/2010 | Cirillo et al. |
| 2011/0112474 | A1 | 5/2011 | Bochenko et al. |
| 2012/0183941 | A1 | 7/2012 | Steinmetz |
| 2013/0191140 | A1 * | 7/2013 | Fotheringham et al. |
| 2013/0233627 | A1 | 9/2013 | Vidal et al. |
| 2014/0140530 | A1 | 5/2014 | Gomes-Casseres et al. |
| 2014/0155827 | A1 | 6/2014 | Ostrander et al. |
| 2015/0126963 | A1 * | 5/2015 | Despa et al. |
| 2015/0296167 | A1 | 10/2015 | Du et al. |
| 2015/0365738 | A1 | 12/2015 | Purvis et al. |
| 2016/0030683 | A1 * | 2/2016 | Taylor et al. |
| 2016/0038675 | A1 | 2/2016 | Estes et al. |
| 2016/0296692 | A1 * | 10/2016 | Agris, III et al. |
| 2017/0032211 | A1 * | 2/2017 | Allerdings et al. |
| 2017/0098058 | A1 * | 4/2017 | McCullough et al. |
| 2017/0136178 | A1 | 5/2017 | Kamen et al. |
| 2017/0189625 | A1 * | 7/2017 | Cirillo et al. |

FOREIGN PATENT DOCUMENTS

| | | |
|---|---|---|
| JP | 2013-521832 | 6/2013 |
| JP | 2013-521963 | 6/2013 |
| JP | 2015-506770 | 3/2015 |
| WO | WO 2010/128493 | 11/2010 |
| WO | WO 2011/117212 | 9/2011 |
| WO | WO 2012/127046 | 9/2012 |
| WO | WO 2013/004843 | 1/2013 |
| WO | WO 2013/120777 | 8/2013 |
| WO | WO 2014/064691 | 5/2014 |

OTHER PUBLICATIONS

PCT International Search Report and Written Opinion in International Application No. PCT/EP2015/064348, dated Sep. 8, 2015, 11 pages.

* cited by examiner

MONITORING SYSTEM AND METHOD

CROSS-REFERENCE TO RELATED APPLICATIONS

This application is a continuation of U.S. patent application Ser. No. 15/320,156, filed Dec. 19, 2016, which is a U.S. national stage application under 35 USC § 371 of International Application No. PCT/EP2015/064348, filed on Jun. 25, 2015, which claims priority to European Patent Application No. 14174717.0 filed on Jun. 27, 2014, the entire contents of which are incorporated herein by reference.

FIELD

The present disclosure relates to a monitoring system and to a method of operating a monitoring system.

BACKGROUND

A variety of diseases exist that require regular treatment by injection of a medicament. Such injections can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage dial and observing the actual dose from a dosage window of the insulin pen. The dose is then injected by inserting the needle into a suited skin portion and pressing an injection button of the insulin pen. To be able to monitor insulin injection, for instance to prevent false handling of the insulin pen or to keep track of the doses already applied or remaining, it is desirable to measure information related to a condition and/or use of the injection device, such as for instance information on the injected insulin type and dose.

For a good treatment of insulin it is necessary to keep a diary to document the day, time and amount of insulin dose. Some patients forget to write the information down or cannot remember when and how much insulin they have injected. Therefore, there is a strong need for further support or automation of this process to make it easier for the patient to keep track of his/her diary.

SUMMARY

A first aspect of the disclosure provides a monitoring system comprising,
    a first device (2) configured to
        capture an image of a medicament dosage indicated by a medicament dispensing device by an image capturing component of the first device;
        display the image of the medicament dosage on a display (21) of the first device; and
        transmit data representing the image of the medicament dosage to a second device; and
    computer code that when executed by a second device causes the second device (100) to:
        receive the data representing the image of the medicament dosage sent by the first device (2);

perform optical character recognition on the data of the medicament dosage thereby to identify the dosage indicated by the medicament dispensing device; and
        make a non-transient record of dosage information based at least in part on the identified medicament dosage.

A system so constructed can provide the advantages of a supplement device that performs OCR and determines delivered dose of medicament but without requiring the hardware needed to perform OCR in the supplemental device. This can reduce the hardware cost of the supplemental device. Moreover, the use of an external device as the second device allows the possibility of a more accurate and reliable OCR process than would be obtainable from OCR recourses that could practically be included in the supplemental device. This is especially the case when the second device comprises a mobile phone such as a smart phone.

The first device may be configured to transmit the data representing the image of the medicament dosage to the second device in response to a user input on the first device or on the second device. This can allow transfer of the data to the second device when there is a change in the use of the dispensing device (e.g. from dialing to injecting or from injecting to injected) or by user input but without utilising communication resources at other times.

The first device may be configured to transmit the data representing the image of the medicament dosage to the second device periodically or continually. This can allow the medicament dosage to be identified and displayed as the user is e.g. dialing and/or injecting medicament, although at the cost of increased communication resource utilisation.

The first device may be configured to capture images of a medicament dosage indicated by the medicament dispensing device and display the images of the medicament dosage periodically or continually. This can allow the user to determine the dialed dose easily and is particularly useful during the dialing and injecting phases of use of the dispensing device.

The first device may be configured to capture images of a medicament dosage indicated by the medicament dispensing device and display the image of the medicament dosage plural times a second. This can allow the user to determine the dialed dose particularly easily and can allow the user to dial the correct dose and dispense the dose more quickly and efficiently than with other arrangements, and may provide an experience similar to the use of a dispensing device that is not fitted with an external device with a recording facility.

The first device may be configured to cause a first display after a first user input on the first device and to cause a second display after a second input on the first device. This can allow a user to determine from the display on the first device whether or not a dose set input, the dwell time a dose delivered input and/or no input has been recorded by the first device.

The non-transient record of dosage information may include a time and/or date information taken from a clock of the first or second device.

The second device may be a mobile telephone.

The computer code may comprise a discreet software application. The software application may be downloadable, for instance from an application market place or store.

The computer code when executed by the second device may cause the second device to display the identified medicament dosage.

A second aspect of the disclosure provides a method of operating a monitoring system, the method comprising,
    a first device (2):

capturing an image of a medicament dosage indicated by a medicament dispensing device by an image capturing component of the first device;

displaying the image of the medicament dosage on a display (21) of the first device; and transmitting data representing the image of the medicament dosage to a second device; and a second device (100):

receiving the data representing the image of the medicament dosage sent by the first device (2);

performing optical character recognition on the data of the medicament dosage thereby to identify the dosage indicated by the medicament dispensing device; and making a non-transient record of dosage information based at least in part on the identified medicament dosage.

BRIEF DESCRIPTION OF THE FIGURES

In the Figures:

FIG. 1b shows a perspective view of some detail of the drug delivery device of FIG. 1a;

DETAILED DESCRIPTION OF SOME EMBODIMENTS OF THE DISCLOSURE

In the following, embodiments of the present disclosure will be described with reference to an insulin injection device. The present disclosure is however not limited to such application and may equally well be deployed with injection devices that eject other medicaments, or with other types of medicament administration devices.

Figure 1A:
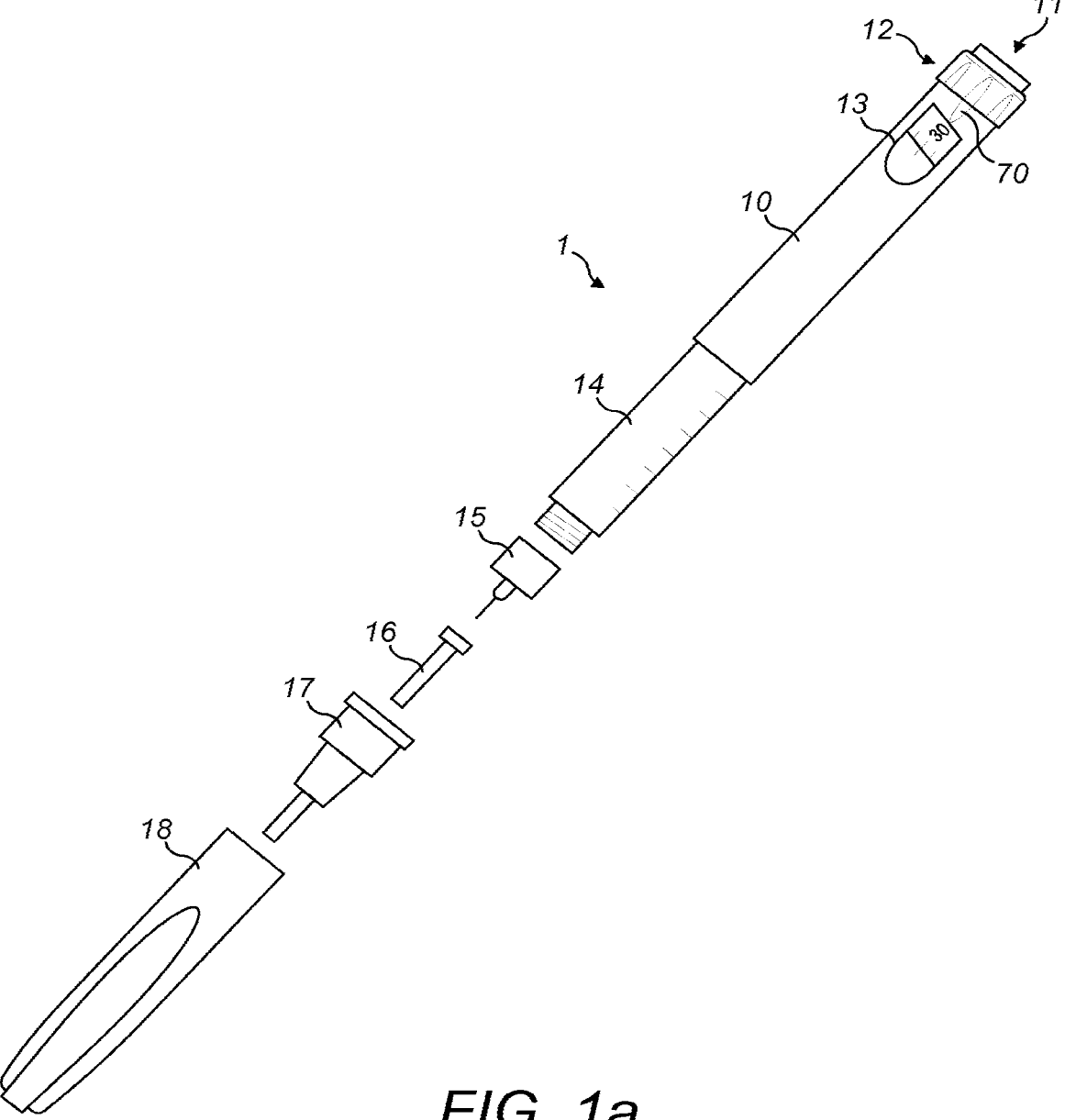
FIG. 1a is an exploded view of a drug delivery device.

FIG. 1a is an exploded view of an injection device 1, which may for instance represent Sanofi's Solostar™ insulin injection pen.

The injection device 1 of FIG. 1a is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage dial 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently. A label (not shown) is provided on the housing 10. The label includes information about the medicament included within the injection device 1, including information identifying the medicament.

Turning the dosage dial 12 causes a mechanical clicker to provide haptic and acoustic feedback to a user. The numbers displayed in dosage window 13 are present on a sleeve by printing and the sleeve is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage dial 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device 1. Nevertheless, differences (e.g. losses) between the ejected doses and the injected doses may of course be taken into account.

Figure 1B:
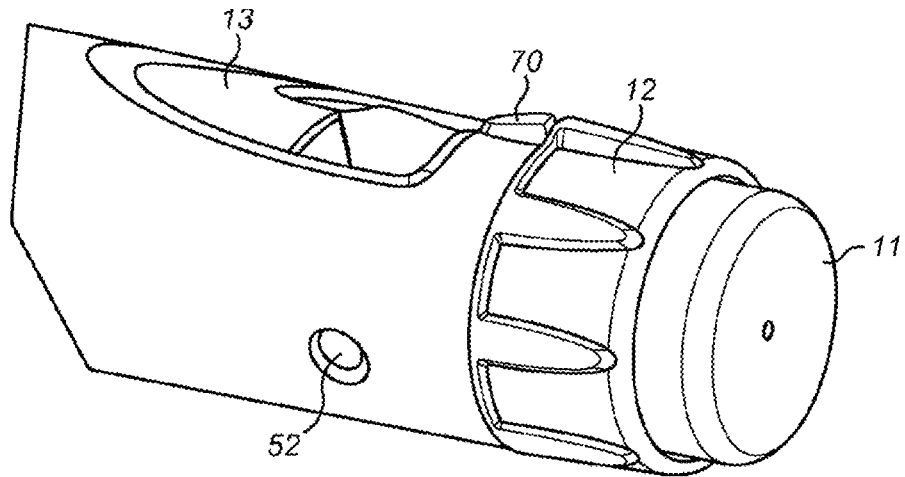

FIG. 1b is a close-up of the end of the injection device 1. This Figure shows a locating rib 70 that is located between the dosage window 13 and the dosage dial 12.

Figure 2A:
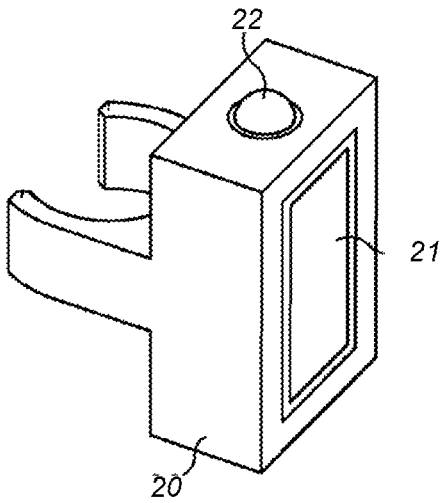
FIG. 2a is an isometric projection of a sensor device or supplementary device according to embodiments of the present disclosure.

FIG. 2a shows an embodiment of a supplementary device 2 to be releasably attached to injection device 1 of FIG. 1a. Supplementary device 2 comprises a housing 20 with a mating unit configured to embrace the housing 10 of injection device 1 of FIG. 1a, so that supplementary device 2 sits tightly on housing 10 of injection device 1, but is nevertheless removable from injection device 1, for instance when injection device 1 is empty and needs to be replaced. FIG. 2a is schematic, and details of the physical arrangement are described below with reference to FIGS. 2b and 2c.

Supplementary device 2 contains optical sensors for gathering information from injection device 1. As described below, a selected dose (also known as a dialed dose) is displayed via LCD display 21 of supplementary device 2. The dosage window 13 of injection device 1 is obstructed by supplementary device 2 when attached to injection device 1.

Supplementary device 2 further comprises at least one user input transducer or switch 22, illustrated schematically as a button type switch. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
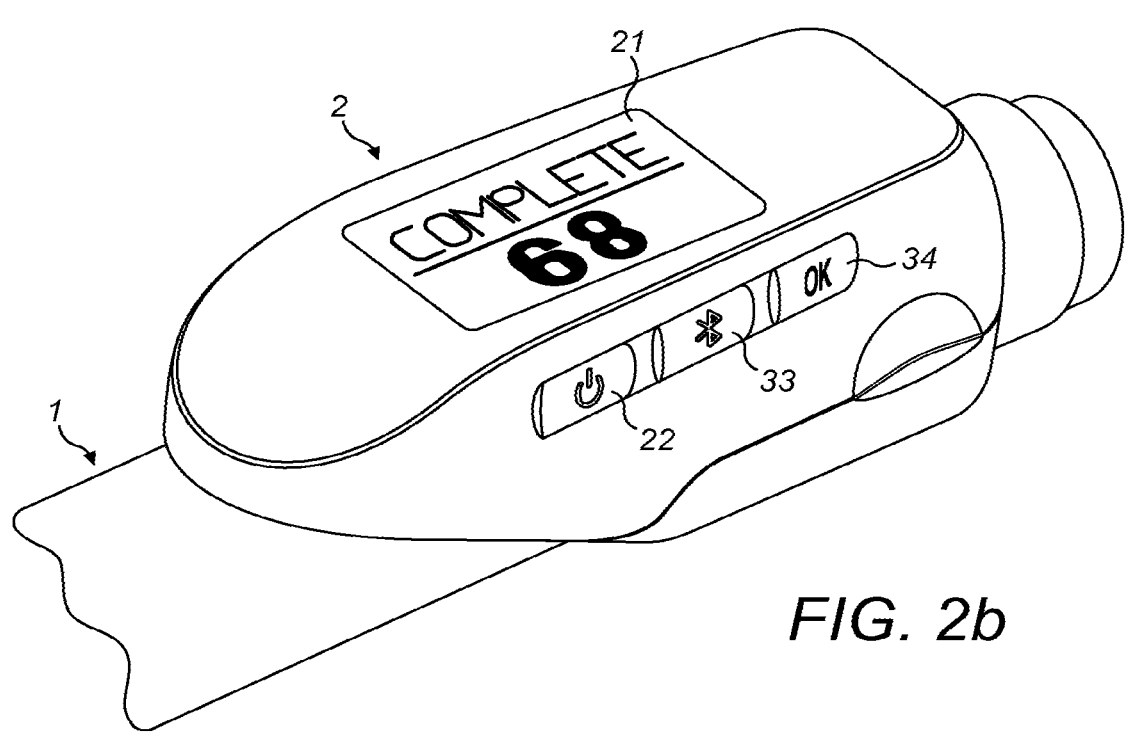
FIG. 2b is an isometric projection of another sensor device or supplementary device according to embodiments of the present disclosure.

FIG. 2b is a schematic illustration of a second embodiment of a supplementary device 2 to be releasably attached to injection device 1 of FIG. 1a. Supplementary device 2 comprises a housing 20 with a mating unit configured to embrace the housing 10 of injection device 1 of FIG. 1a, so that supplementary device 2 sits tightly on housing 10 of injection device 1, but is nevertheless removable from injection device 1.

Information is displayed via LCD display 21 of supplementary device 2. The dosage window 13 of injection device 1 is obstructed by supplementary device 2 when attached to injection device 1.

Supplementary device 2 further comprises three user input transducers, buttons or switches. A first button 22 is a power on/off button, via which the supplementary device 2 may for instance be turned on and off. A second button 33 is a communications button. A third button 34 is a confirm or OK button. The buttons 22, 33, 34 may take any suitable form. These input buttons 22, 33, 34 allow a user to turn on/off supplementary device 2, to trigger actions (for instance to cause establishment of a connection to or a pairing with another device, to trigger transmission of information from supplementary device 2 to another device), to confirm something, and/or to display information on the LCD display 21.

Figure 2C:
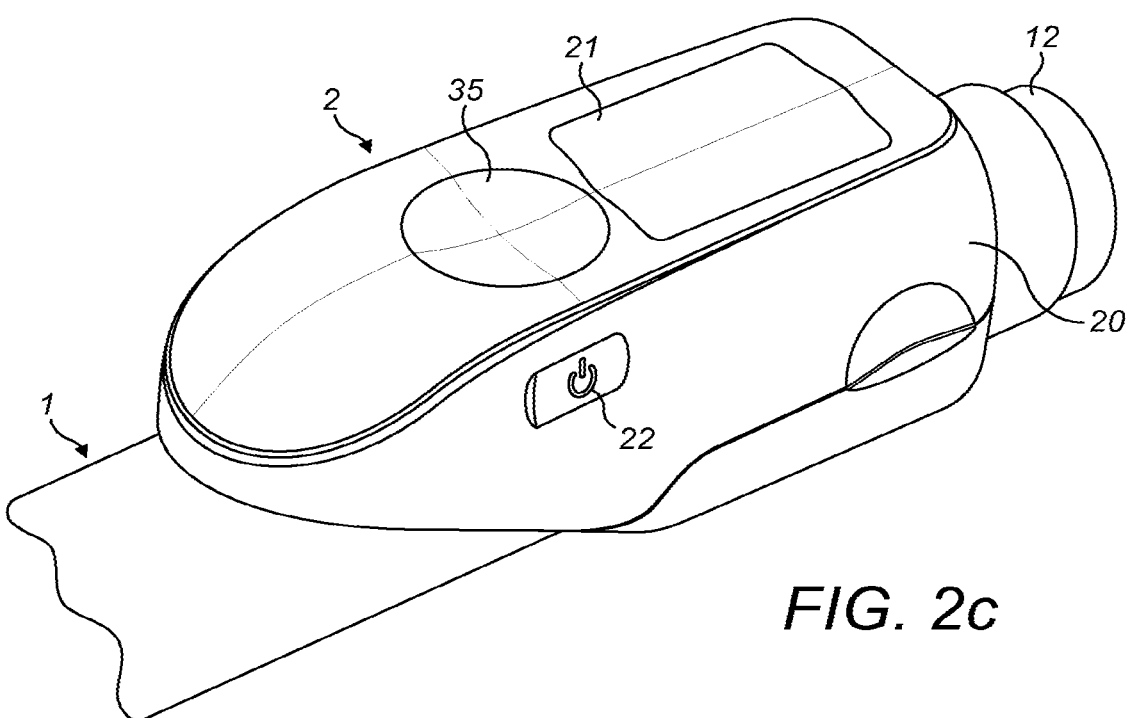
FIG. 2c is an isometric projection of a still further sensor device or supplementary device according to embodiments of the present disclosure.

FIG. 2c is a schematic illustration of a third embodiment of a supplementary device 2 to be releasably attached to injection device 1 of FIG. 1a. Supplementary device 2 comprises a housing 20 with a mating unit configured to embrace the housing 10 of injection device 1 of FIG. 1a, so that supplementary device 2 sits tightly on housing 10 of injection device 1, but is nevertheless removable from injection device 1.

Information is displayed via LCD display 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of image data information from supplementary device 2 to the mobile device 100. This multi-function touch-sensitive input transducer 35 removes the need for the communications button 33 or a confirm button 34 and simplifies the configuration of the supplementary device 2. Such a multi-function transducer 35 may be mechanical instead of being touch-sensitive.

The mobile device 100 may display the dose dialed into the injection device 1. This can allow the user to check the dialed dose calculated by the mobile device 100 against the dose displayed on the LCD display 21 of the supplementary device 2. The mobile device 100, through the medicament administration monitoring application 110, may allow the user to vary the dialed dose from that calculated by the optical character recognition process. This can allow more accurate recordal of medicament administration. The mobile device 100 may alternatively or additionally require the user to confirm the displayed dose, or allow the user to confirm that the displayed dose is the dialed dose.

Figure 3:
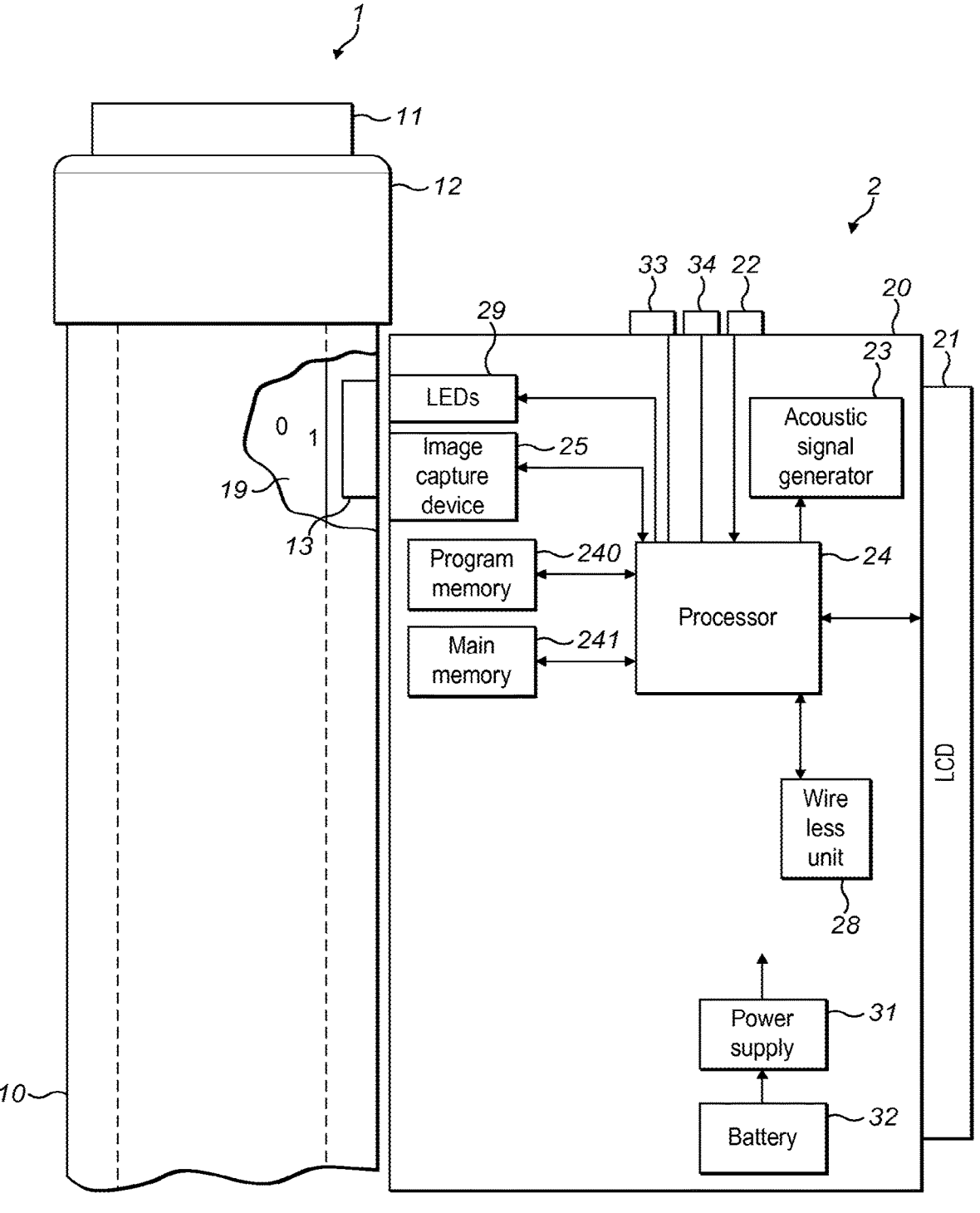
FIG. 3 is a schematic view of a sensor device as in FIGS. 2 a, b, c attached to a drug delivery device and showing internal components of the sensor device.

FIG. 3 shows a schematic view of the supplementary device 2 of FIG. 2b or 2c in a state where it is attached to injection device 1 of FIG. 1a.

With the housing 20 of supplementary device 2, a plurality of components is contained. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Program memory 240 may for instance be a Read-Only Memory (ROM) or Flash memory, and main memory may for instance be a Random Access Memory (RAM).

In embodiments such as those shown in FIG. 2b, processor 24 interacts with the first button 22, via which supplementary device 2 may for instance be turned on and off. The second button 33 may be used to trigger establishment of a connection to another device, or to trigger a transmission of information to another device. The third button 34 can be used to acknowledge information presented to a user of supplementary device 2.

In embodiments such as those shown in FIG. 2c, two of the buttons 33, 34 may be omitted. Instead, one or more capacitive sensors or other touch sensors are provided.

Processor 24 controls a display 21, which is presently embodied as a Liquid Crystal Display (LCD). LCD display 21 is used to display information to a user of supplementary device 2, for instance on present settings of injection device 1, or on a next injection to be given. LCD display 21 may also be embodied as a touch-screen display, for instance to receive user input.

Processor 24 also controls an image capture device 25 that is configured to capture images of the dosage window 13, in which a currently selected (dialed) dose is displayed (by way of numbers, characters, symbols or glyphs present on the sleeve 19 contained in injection device 1, which numbers are visible through the dosage window 13). The image capture device 25 may be a camera of any suitable type.

Processor 24 also controls one or more light-sources such as light emitting diodes (LEDs) 29 to illuminate the scene that is visible through the dosage window 13, in which a currently selected dose is displayed. A diffuser may be used in front of the light-sources, for instance a diffuser made from a piece of acrylic glass or polycarbonate. Furthermore, the optical sensor may comprise a lens system, for instance including two aspheric lenses. The magnification ratio (image size to object size ratio) may be smaller than 1. The magnification ratio may be in the range of 0.05 to 0.5.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth or Bluetooth Low Energy transceiver. Alternatively, wireless unit 28 may be substituted or complemented by a wired unit configured to transmit and/or receive information to/from another device in a wire-bound fashion, for instance via a cable or fibre connection.

The supplementary device 2 of FIG. 3 is thus capable of capturing information related to a condition and/or use of injection device 1. This information is displayed on the display 21 for use by the user of the device and some of the information is transmitted wirelessly to another device.

Figure 4:
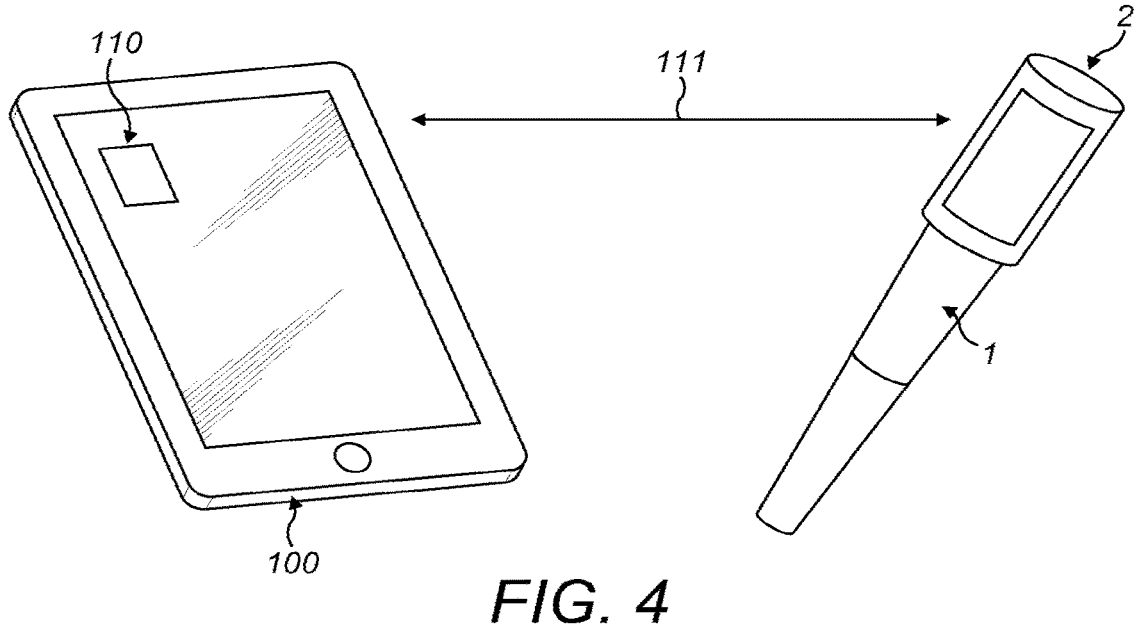
FIG. 4 shows the FIG. 1a injection device 1 fitted with a FIG. 2 a, b, c, sensor device and wirelessly communicating with a mobile terminal.

FIG. 4 shows the supplementary device and injection device 1 being used in conjunction with a mobile device 100 such as a smartphone. The mobile device 100 is programmed in a suitable way, for instance by being provided with a suitable software application 110.

In brief, the system of the supplementary device 2 and the mobile device 100 function to display and record medicament dosage when the injection device 1 is used. The supplementary device 2 communicates with the mobile device 100 using a communication interface 28 e.g. Bluetooth. The user interacts primarily with the supplementary device 2. The mobile device 100 serves primarily to provide information to the user and to record the user's injection history. The supplementary device 2 transmits data representing an image captured by the camera 25 of the scene through the dosage window 13 to the mobile device 100 via a predefined communication channel 111 (see FIG. 4). The mobile device 100 performs Optical Character Recognition (OCR) processing to identify the selected medicament dosage from the image data received from the supplementary device 2. The mobile device 100 may identify the selected dose before and after dispensing, calculate the administered dosage, display the administered dose and makes a record of the administered dosage information. A time stamp may be added to the dosage information. A more detailed explanation of how the system is configured and functions is described below.

The camera image taken is stored in the memory 241 of the supplementary device 2 together with a time stamp and information about the drug type.

Figure 5:
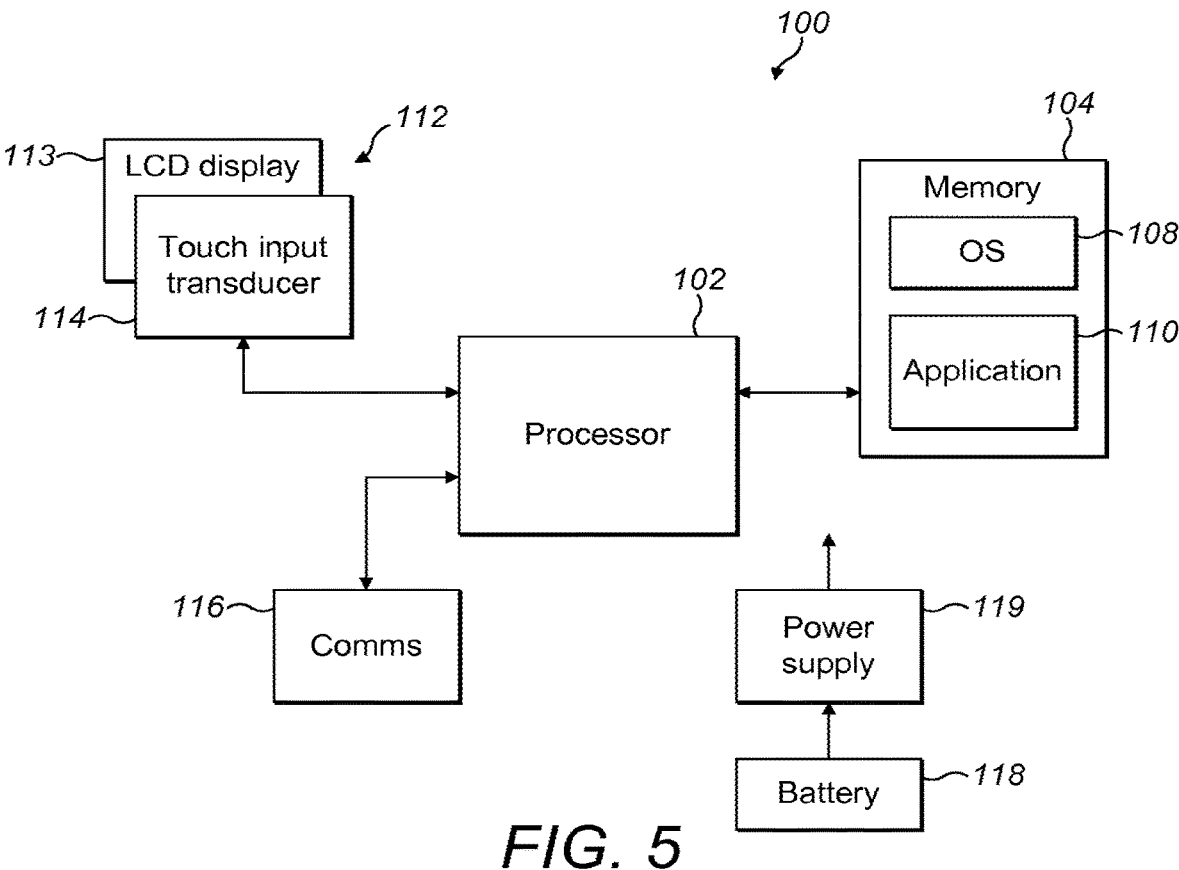
FIG. 5 is a schematic view of the mobile terminal of FIG. 4 and showing internal components of the mobile terminal 100.

Some of the internal components of the mobile device 100 are shown in FIG. 5. The mobile device 100 includes a processor 102. The processor 102 controls operation of the other hardware components of the mobile device 100. The processor 102 and other hardware components may be connected via a system bus (not shown). Each hardware component may be connected to the system bus either directly or via an interface.

The mobile device 100 comprises a memory 104, i.e. a working or volatile memory, such as Random Access Memory (RAM), and a non-volatile memory. The non-volatile memory stores an operating system 108 and a medicament administration monitoring function 110, which advantageously is a distinct application, as well as storing data files and associated metadata. The medicament administration monitoring application 110 may be provided in the mobile device 100 on manufacture or it may be down loaded into the mobile device 100 by a user, for instance from an application market place or application store.

The mobile device 100 comprises a display 112 (for instance an LCD, TFT (thin film transistor), OLED (organic light emitting diode), ePaper). The display may be a touch sensitive display having a display part 113 and a tactile interface part 114. The mobile device 100 also includes a communications interface 116, such as a Bluetooth interface. The mobile device 100 also houses a battery 118 to power the mobile device 100 by a power supply 119.

The processor 102 is configured to send and receive signals to and from the other components in order to control operation of the other components. For example, the processor 102 controls the display of content on display 112 and receives signals as a result of user inputs from tactile interface 114. The display 112 may be a resistive touch screen or capacitive touch screen of any kind. The display may alternatively not be a touch screen. For instance it may be a liquid crystal display (LCD).

The mobile device 100 may be a mobile phone, PDA or tablet computer of any kind, or it may be a BGM (blood glucose meter) device. Other standard or optional components of the mobile device 100, such as transceivers and cameras, are omitted. The processor 102 may be an integrated circuit of any kind. The processor 102 may access RAM in order to process data and may control the storage of data in memory 104. Memory 104 may be a non-volatile memory of any kind such as a Read Only Memory (ROM), a flash memory and a magnetic drive memory. The RAM may be a RAM of any type, for example Static RAM (SRAM), Dynamic RAM (DRAM) or a Flash memory.

The processor 102 operates under control of the operating system 108. The operating system 108 may comprise code relating to hardware such as the display 112 and communications interface 116, as well as the basic operation of the mobile device 100. The operating system 108 may also cause activation of other software modules stored in the memory 104, such as the medicament administration monitoring function 110.

Figure 6:
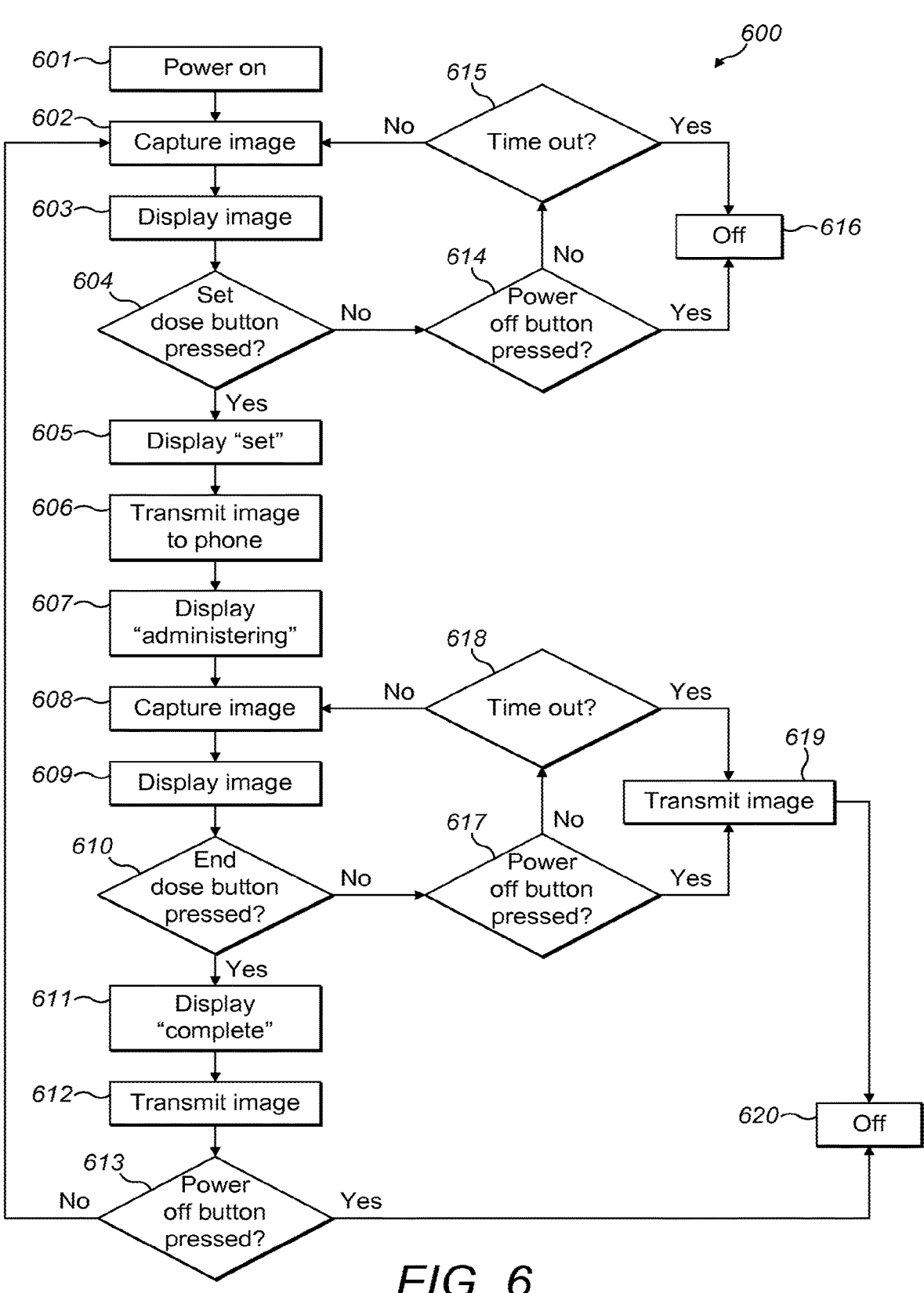
FIG. 6 is a flow chart showing operation of the FIGS. 2 a, b, c sensor device or supplementary device according to embodiments of the disclosure.
Figure 7:
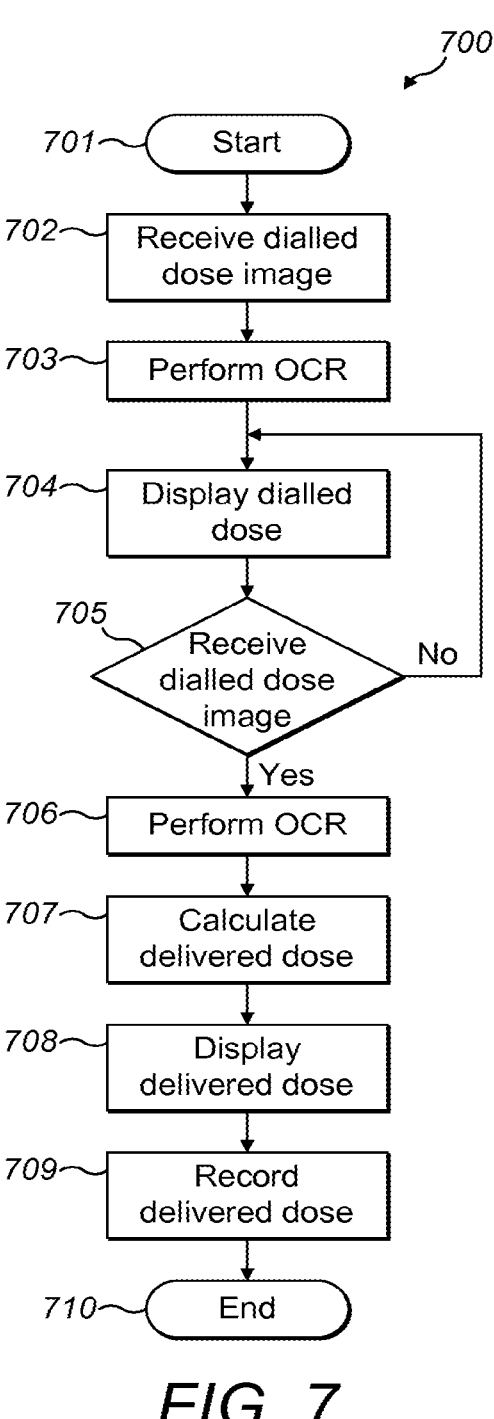
FIG. 7 is a flow chart showing operation of the FIG. 4 mobile terminal according to embodiments of the disclosure.

FIG. 6 and FIG. 7 are flow charts illustrating operation of the supplementary device 2 and the mobile device 1a respectively. The flow charts illustrate how the supplementary device 2 and the mobile device 100 interact and operate as a system when the injection device 1 is being utilised. The steps of FIG. 6 are performed by the processor 24 of the supplementary device 2 under control of the software stored in the memory 240.

In FIG. 6, the operation 600 starts for instance when the supplementary device 2 is turned on or is otherwise activated at 601. In a step 602, the processor 24 controls the camera 25 to capture an image of the current dosage displayed on the number sleeve of the injection device 1, as is visible through the dosage window 13 of the injection device 1. This image is then caused to be displayed on the LCD display 21 of the supplementary device 2 in a step 603. The image is processed to some degree before display. In particular, the image may be resized so as to fit the LCD display 21. In the case of the camera having more pixels than the LCD display 21, resizing involves downscaling the image. Downscaling may comprise for instance selecting only some pixels of the captured image for display (and not displaying others), or averaging groups of pixels. The image advantageously is displayed in greyscale. This avoids the need for the supplementary device to perform processing of the image to detect boundaries of characters etc. It also reduces the possibility that the displayed image is significantly different from the scene in front of the camera 25. Alternatively, the image may be displayed in black and white (without greyscale), or colour.

In a step 604, it is checked whether a user input, indicating that a required dosage has been set, has been provided for instance by a button press on the supplementary device 2. If no button press is detected, the operation proceeds to step 614, where it is determined if the power button 22 has been pressed. On a negative determination, the operation proceeds to step 615, where it is determined if there is a time out condition. The time out condition occurs when a timer that is reset and started when the supplementary device 2 powers on or when it is detected that the power button 22 has been pressed has expired. A suitable value for the timer may be 60 or 120 seconds. On a negative determination from step 615, the operation returns to step 602, where a next image is captured and then displayed at step 603.

On a positive determination from step 614 or 615, indicating that the time out condition has occurred or the user has pressed the power button 22, the supplementary device 2 powers off and the operation ends at step 616. This helps to minimise power consumption of the supplementary device but without impinging on operation when the user is interacting with the supplementary device 2 or the injection device 1.

The sequence from step 604 to step 614 to step 615 then to step 602 causes the supplementary device 2 to remain capturing images and displaying them until either the power button 22 is pressed or the time out condition occurs or until it is determined at step 604 that the confirm or OK button 34 to set dose has been pressed. This loop allows the user to set the required dosage by turning the dosage dial 12 on the injection device 1 and reading the image containing the current dosage information displayed on the LCD display 21. Therein, if the power off button 22 press is detected in step 614, the processor 24 turns the supplementary device 2 off. If no power off button 22 press is detected but a timeout is reached in step 615, the processor 24 turns the supplementary device 2 off.

When the processor 24 detects a confirm or OK button 34 press by the user to confirm that a required dosage has been set in 604, at step 605 a dose set condition is indicated on the display 21 by the processor 24. The processor 24 then controls the wireless unit 28 to transmit data representing the image of the currently dialed dose to the mobile device 100 in step 606 for further processing. Advantageously, the data representing the image that is transmitted is the whole image, relating to all of the pixels and including a greyscale value for each pixel. Alternatively, there may be some pre-processing of the image before transmission. However, no optical character recognition is performed on the image before transmission. The transmitted data represents an image and is not indicative of a set dose other than the data being an image of the dose dialed into the injection device 1 at the time the image was captured. The image may be compressed in a lossy or lossless manner before transmission time and communication resave initialisation.

In a step 607, the processor 24 controls the LCD display 21 to display "Administering". At this stage, the user may be administering (delivering) the dose dialed into the injection device 1 before the confirm or OK button 34 to set dose was detected to be pressed at step 604.

Steps 605 and 607 may be performed in the other order, or they may be performed in parallel with one another.

In a step 608, the processor 24 controls the camera to capture an image in front of the camera, which indicates the current dosage as visible in the dosage window 13. This image is then displayed on the LCD display 21 of the device in a step 609. Steps 608 and 609 are the same as steps 602 and 603 as described above.

When the injection process is complete, the user is expected to press a confirm or OK button 34 on the supplementary device 2 to indicate "End dose" to the processor 24 at step 610. If the processor 24 at step 610 detects a confirm or OK button 34 press that indicates the "End dose", it controls the LCD display 21 to display "Complete" in a step 611. In a step 612, the current image is transmitted to the mobile device 100. Steps 612 and 611 may be performed in the other order, or they may be performed in parallel.

Next it is determined at step 613 whether the power button 22 has been pressed. If it is detected at step 613 that the power button 22 has been pressed, the supplementary device 2 then turns off at step 620. If not, it returns to step 602, where the image in front of the camera 25 is captured before being displayed at step 603. This repeats until the time out condition occurs or the power button 22 is pressed.

If no confirm or OK button 34 press is detected in step 610 the operation proceeds to step 617, where it is determined if the power button 22 has been pressed. On a negative determination, the operation proceeds to step 618, where it is determined if there is a time out condition. The time out condition occurs when a timer that is reset and started when the supplementary device 2 powers on or when it is detected that the power button 22 has been pressed has expired. A suitable value for the timer may be 60 or 120 seconds. On a negative determination from step 618, the operation returns to step 608, where a next image is captured and then displayed at step 609.

On a positive determination from step 617 or 618, indicating that user has pressed the power button 22 or the time out condition has occurred, the supplementary device 2 transmits the current image to the mobile device 100 and then powers off ending the operation at step 620. This helps to minimise power consumption of the supplementary device 2 but without impinging on operation when the user is interacting with the supplementary device 2. Further, transmitting the current image to the mobile device 100 at this stage i.e. before power off also ensures that the final dosage information is recorded on the mobile device 100. This scenario could arise as a result of the user forgetting to press the confirm or OK button 34 at step 610 to indicate "End dose" to the processor 24 after the injection process is complete.

FIG. 7 is a flowchart of the method steps that are performed by the mobile device 100 in conjunction with the method steps performed by the supplementary device 2 in FIG. 6. In FIG. 7, the flowchart 700 starts at step 701 for instance when the supplementary device 2 is turned on or is otherwise activated. Following transmission of the image data in step 606 of FIG. 6, in step 702 the mobile device 100 receives the image data. This constitutes image data containing information of the medicament dosage set by the user and sent from the supplementary device 2. In step 703, the mobile device 100 performs optical character recognition processing on the received data. This can be performed in any suitable way. The optical character recognition involves processing the image of the number sleeve that is in the scene in front of the camera 25 of the supplementary device 2 to identify the dose that is dialed into the supplementary device 2. The result is a number that represents the dialed dose, for instance in IU. The number may be provided by the optical character recognition process as an integer or it may be between integer numbers if the optical character recognition process is suitably configured.

After the dialed dose has been determined through the optical character recognition process, the mobile device 100 is controlled by the medicament administration monitoring application to display the identified dialed or set dosage information to the user on the display 113 at step 704. The dialed dosage is displayed to the user on the display 113 along with an indication that it is the dialed dose, not the dispensed dose, that is being displayed. The indication may take any suitable form. For example, the indication may comprise the word "selected", "dialed", or "set", or any other text form suitable and/or common to indicate to a user that it is the dialed dose, not the dispensed dose that is being displayed. The text format comprises also any translation into a language that is being set in the device. The indication may comprise an image, such as a pictogram suitable and/or common to indicate to a user that it is the dialed dose, not the dispensed dose that is being displayed. The image indication may be provided as alternative or in combination with a text-based indication.

At step 705, the mobile device 100 determines whether a delivered dose image has been received from the supplemental device 2. If no delivered dose image data has been received, the mobile device 100 returns to step 704, where the dialed dose is again displayed. This repeats until a delivered dose image is received from the supplemental device 2.

If the mobile device 100 determines at step 705 that it has received delivered dose image data containing information of the final dose after the injection has been administered, it performs optical recognition processing on the delivered dose image data at step 706, in any suitable way. This results in a number that indicates the dialed dose after injection/delivery. The mobile device 100 then calculates at step 707 the delivered dose using the dialed and final dose information received from the supplementary device 2, in particular by subtracting the dose shown after delivery from the dose shown before delivery. Alternatively, if it is detected or assumed that the final dose is zero, this can be omitted. The calculated delivered dose information is displayed to the user on the mobile device 100 by the medicament administration monitoring application 110 in a step 708. The delivered dose information is then stored in the memory 104 of the mobile device 100 at step 709 before the operation ends at step 710.

The storage of the dose information at step 709 constitutes a record of the medicament administration. The record includes the time or time and date of administration, taken from the internal clock of the mobile device 100, the dose delivered and optionally other information provided by the user such as a blood glucose measurement taken before the medicament delivery, the type of medicament etc. This allows a complete record of the medicament intake of the user to be recorded by the mobile device 100 without requiring the user to enter the dialed, post-delivered or delivered dose.

Operation of the system will now be described from the users perspective.

The user begins by turning on the supplementary device 2 (which requires one press of the power button 22) and opening or initiating the medicament administration monitoring application 110 on the mobile device 100. Next, a communications channel 111 between the supplementary device 2 and the mobile device 100 is established. This can be achieved by the user pressing the communications button 33 on the supplementary device 2. In this case, the user may need to interact with the medicament administration monitoring application 110 on the mobile device 100 to allow the connection to be established, or connection may be automatic if the devices have been suitably configured, for instance through Bluetooth pairing. Alternatively, a communications link between the supplementary device 2 and the mobile device 100 may be established without requiring any user input, for instance in response to the supplementary device 2 being powered on. The receipt by the mobile device 100 of a signal from the supplemental device 2 may cause the mobile device 100 to launch the medicament administration monitoring application 110 on the mobile device 100.

When turned on, the current dosage on the injection device 1 is displayed to the user on the supplementary device 2 LCD display 21. The user can now set the required medicament dosage by turning the dosage dial 12 on the injection device 1 while reading the current dosage reading on the LCD display 21.

When the required medicament dosage is set, the user presses the confirm or OK button 34 on the supplementary device 2. At this time, the supplementary device 2 is displaying the medicament dose on the LCD display 21. The medicament administration monitoring application 110 on the mobile device 100 then displays the dosage set by the user on the mobile device 100 display. The user is now able to double-check that the correct dose has been recognised by the mobile device 100. However, the user does not need to check the mobile device 100 at this stage.

After a short time, the display of the LCD display 21 on the supplementary device 2 then changes to indicate that the dose has been set. Before or after this change in display, the user can start to inject the medicament. As the medicament is administered, the dosage reading on the LCD display 21 changes as the dose indicated on the part of the number sleeve of the injection device 1 in front of the camera changes. When the injection process is complete, the user may press the confirm or OK button 34 again or may allow the timer to timeout. The supplementary device 2 LCD display 21 then changes to display "Complete". The supplementary device 2 at this time displays the remaining dosage in the injection device 1 on the LCD display 21. The remaining dose typically is zero but it may be higher if the user did not complete the injection.

Next, the mobile medicament administration monitoring application 110 displays the administered dose on the mobile device display, and may also display the final dialed dose to allow the user to check that the mobile device 100 has registered the correct final dialed dose. The medicament administration monitoring application 110 on the mobile device 100 also displays a message indicating that a record relating to the administered dosage has been created and stored.

Further, advantageously HDR images are captured by the image capturing device 25 in order to contribute to a high contrast of the dosage information so that binarization and OCR calculation in the mobile device 100 is improved.

The scope of the disclosure is not limited to the above-described embodiments and various alternatives will be envisaged by the skilled person. Further alternatives will now be described.

In FIG. 2b, the communications button 33 can be omitted from the supplementary device. When the power button 22 is pressed, the supplementary device 2 can turn on and automatically establish connection with the mobile device 100. This simplifies the function of the supplementary device 2 and allows it to have fewer hardware buttons.

At step 608, the mobile device 100 may display both the dose dialed into the injection device 1 after delivery and the calculated dose. This can allow the user to check the dialed dose calculated by the mobile device 100 against the dose displayed on the LCD display 21 of the supplementary device 2. The mobile device 100, through the medicament administration monitoring application 110, may allow the user to vary the dialed dose from that calculated by the optical character recognition process. This can allow the record of medicament administration recorded in the mobile device 100 to be more accurate than otherwise.

Instead of transmitting image data only in response to a user input on the supplementary device 2, operation may differ. For instance, image data may be transmitted continually or frequently to the mobile device 100, and the mobile device may then display the dialed dose as dialing occurs and/or as injecting occurs. In this case, the user input indicating that the dose has been set may be made on the mobile device 100 instead of on the supplementary device 2. In this case, the user can check the dialed dose indicated on the mobile device 100 (which has been subjected to optical character recognition) against the image displayed on the LCD display 21 of the supplementary device 2. Similarly, the user indicating that the injection has completed may be made on the mobile device 100 instead of the supplemental device 2. Alternatively, both the supplemental device 2 and the mobile device 100 may be configured to receive the dose set user input and/or the injection complete user input, thereby allowing the user more choices for using the system.

The indication that the dose has been set may be made alternatively or additionally on the mobile device. The same applies to the indication that the dose has been delivered. In the above, the image data is sent to the mobile device during the dose delivery process.

Alternatively, the image data may be stored in the memory 241 of the supplementary device 2 and transmitted to the mobile device 100 at a later time, for instance minutes, hours or tens of hours later. Transmission to the mobile device may include images for two or more dose deliveries.

The supplemental device 2 may include a means for detecting the medicament included in the injection device 1. This may take the form of a colour sensor that is configured to detect the colour of a label on the injection pen, the label colour indicating the type of medicament contained.

The invention claimed is:

1. A smartphone, comprising:
a display;
a processor;
a wireless communications interface based on radio transmissions; and
a memory configured to store a medicament administration monitoring application,
wherein the processor is configured to:
execute the medicament administration monitoring application,
establish a connection between the smartphone and an external sensor device using a radio frequency transmission, wherein the external sensor device is attached to a medicament dispensing device, the medicament dispensing device being physically decoupled from the smartphone and configured to inject a medicament into a patient through a needle,
receive information associated with the medicament delivered to the patient from the external sensor device,
generate, using the medicament administration monitoring application, a record based on the medicament information,
store the record of the medicament information in the memory,
display the medicament information on the display,
receive, in real-time and from the external sensor device multiple times a second, information indicative of a medicament dose that is being dialed into the medicament dispensing device as dialing occurs and a medicament dose that has been delivered by the medicament dispensing device to the patient, and
update, in real-time and multiple times a second, the medicament information displayed on the display in accordance with the received information.

2. The smartphone according to claim 1, wherein the processor is configured to establish the connection between the smartphone and the external sensor device automatically.

3. The smartphone according to claim 1, wherein the processor is configured to establish the connection between the smartphone and the external sensor device in response to an input on the smartphone.

4. The smartphone according to claim 1, wherein the processor is configured to execute the medicament administration monitoring application in response to a user input applied to the smartphone.

5. The smartphone according to claim 1, wherein the processor is configured to execute the medicament administration monitoring application automatically when a signal is received from the external sensor device.

6. The smartphone according to claim 1, wherein the record includes at least one of date information, a volume of medicament, and a type of medicament.

7. The smartphone according to claim 1, wherein the displayed medicament information comprises a delivered volume.

8. The smartphone according to claim 1, wherein the processor is configured to cause the display to display an indication that the record has been created or stored, and the indication is a text or an image.

9. The smartphone according to claim 1, wherein the smartphone is configured to receive a user input indicating that a medicament delivery process is complete and control the display to display an indication that the medicament delivery process is complete.

10. The smartphone according to claim 1, wherein the smartphone is configured to store, in the memory, a diary containing a plurality of records tracking a plurality of medicament deliveries based on received data.

11. A monitoring system, comprising:
a sensor attachable to a delivery device containing a medicament, wherein the sensor is configured for a radio frequency transmission of data representing a medicament delivered by the delivery device; and
a smartphone for receiving, storing, and displaying data received from the sensor, the sensor and the delivery device being physically decoupled from the smartphone,
wherein the smartphone comprises a display, a processor, a wireless communications interface, and a memory, wherein the smartphone is configured to:
receive the radio frequency transmission of data from the sensor,
store a record including a plurality of medicament deliveries based on the received data,
display at least part of the record,
display medicament information on the display,
receive, in real-time and from the sensor multiple times a second, information indicative of a medicament dose that is being dialed as dialing occurs and a medicament dose delivered to a patient, and
update, in real-time and multiple times a second, the medicament information displayed on the display in accordance with the received information.

12. The system of claim 11, wherein the delivery device has a distal end having a needle.

13. The system of claim 11, wherein the smartphone is configured to store, in the memory, a diary containing a plurality of records tracking a plurality of medicament deliveries based on the received data.

14. A mobile phone, comprising:
a display;
a processor;
a wireless communications interface; and
a memory communicatively coupled with the processor,
wherein the processor is configured to:
establish, via the wireless communications interface, a communications link between the mobile phone and an external supplementary device, wherein the external supplementary device is releasably coupled to a medicament dispensing device, the medicament dispensing device being physically decoupled from the mobile phone and configured to inject a dose of medicament into a patient through a needle, receive, from the external supplementary device, dosage information associated with the dose of medicament administered to the patient, generate a record of medicament administration based on the dosage information, display medicament information on the display, receive, in real-time and from the external supplementary device multiple times a second, information indicative of a medicament dose that is being dialed as dialing occurs and a medicament dose that has been delivered to the patient, update, in real time and multiple times a second, the medicament information displayed on the display in accordance with the received information.

15. A method of operating a monitoring system, comprising:

executing, by a processor of a smartphone of the monitoring system, a medicament administration monitoring application preloaded in a memory of the smartphone, establishing, by the processor of the smartphone, a wireless communication link between the smartphone and an external sensor device of the monitoring system using a radio frequency transmission, wherein the external sensor device is attached to a delivery device containing a medicament, the delivery device being physically decoupled from the smartphone, and wherein the external sensor device is configured for a radio frequency transmission of data associated with a medicament delivered by the delivery device, transmitting the data associated with the medicament from the external sensor device to the smartphone, executing, by the processor of the smartphone, the medicament administration monitoring application to generate a record based on the data associated with the medicament delivered by the delivery device, storing the record in the memory of the smartphone, displaying medicament information on a display of the smartphone, receiving, in real-time and from the external sensor device multiple times a second, information indicative of a medicament dose that is being dialed as dialing occurs and a medicament dose that has been delivered to a patient, and updating, in real-time and multiple times a second, the medicament information displayed on the display in accordance with the received information.

16. The method of claim 15, wherein the wireless communication link uses near-field communication.

17. The method of claim 15, further comprising displaying an indication of the data on the display of the smartphone.

18. The method of claim 15, further comprising downloading the medicament administration monitoring application to the smartphone from an application marketplace or an application store.

19. The method of claim 15, further comprising preprocessing of the data associated with the medicament within the external sensor device.

20. The method of claim 19, further comprising additional processing of the data associated with the medicament within the smartphone.

21. The method of claim 15, further comprising storing, in the memory of the smartphone, a diary containing a plurality of records tracking a plurality of medicament deliveries based on received data.

* * * * *